United States Patent [19]

Matsumoto et al.

[11] Patent Number: 4,567,305
[45] Date of Patent: Jan. 28, 1986

[54] PROCESS FOR CONTINUOUS HYDROFORMYLATION OF ALLYL ALCOHOL

[75] Inventors: Mitsuo Matsumoto, Kurashiki; Shinichi Miura, Nakajyo; Koichi Kikuchi, Toyonaka; Masuhiko Tamura, Kurashiki; Hidetaka Kojima; Kunio Koga, both of Himeji; Shigeru Yamashita, Arai, all of Japan

[73] Assignees: Kuraray Company, Ltd.; Daicel Chemical Industries, Ltd., both of Okayama, Japan

[21] Appl. No.: 621,016

[22] Filed: Jun. 15, 1984

[30] Foreign Application Priority Data

Jun. 24, 1983 [JP] Japan ................................ 58-114549

[51] Int. Cl.$^4$ ............................................ C07C 45/50
[52] U.S. Cl. .................................... 568/454; 568/902; 568/909
[58] Field of Search ............... 568/909, 883, 454, 489, 568/902

[56] References Cited

U.S. PATENT DOCUMENTS

| 4,148,830 | 4/1979 | Pruett et al. ........................ 568/454 |
| 4,215,077 | 7/1980 | Matsumoto et al. ................ 568/496 |

FOREIGN PATENT DOCUMENTS

| 2715685 | 10/1977 | Fed. Rep. of Germany ...... 568/454 |
| 1338225 | 11/1973 | United Kingdom ................ 568/454 |
| 1493154 | 11/1977 | United Kingdom ................ 568/496 |

Primary Examiner—Werren B. Lone
Attorney, Agent, or Firm—Flynn, Thiel, Boutell & Tanis

[57] ABSTRACT

Allyl alcohol is hydroformylated with a gaseous mixture of hydrogen and carbon monoxide, in an aromatic hydrocarbon, in the presence of a rhodium complex and a trisubstituted phosphine, to form hydroxybutyraldehydes which are separated from the reaction mixture within an aqueous medium. The carbon monoxide partial pressure, the rate of consumption of carbon monoxide, the rate at which the carbon monoxide is dissolved in the reaction mixture, reaction temperature and the viscosity of the reaction mixture are selected and controlled in an interrelated way to give a high yield of 4-hydroxybutyraldehyde and reduced catalyst consumption.

6 Claims, 3 Drawing Figures

PROCESS FOR CONTINUOUS HYDROFORMYLATION OF ALLYL ALCOHOL

This invention relates to a process for hydroformylating allyl alcohol. More particularly, it relates to a process for the continuous hydroformylation of allyl alcohol, which process is suitable for practical industrial use.

A known process for the hydroformylation of allyl alcohol comprises hydroformylating allyl alcohol with a gaseous mixture of hydrogen and carbon monoxide, in an organic solvent, in the presence of a rhodium complex as a catalyst, then extracting hydroxybutyraldehydes from the resulting hydroformylation reaction mixture with water and recycling the extraction residue to the hydroformylation reaction step as a catalyst-containing solution. See British Pat. No. 1 493 154.

The hydroxybutyraldehydes obtainable in the hydroformylation of allyl alcohol include 4-hydroxybutyraldehyde (hereinafter abbreviated as HBA) and 3-hydroxy-2-methylpropionaldehyde (hereinafter referred to as HMPA). These can easily be converted to 1,4-butanediol (hereinafter abbreviated as 1,4-BG) and 2-methyl-1,3-propanediol (hereinafter abbreviated as MPG), respectively, by hydrogenation.

In the hydroformylation of allyl alcohol, two by-products are formed, in addition to the above-named two hydroformulation products. One by-product is propionaldehyde (hereinafter abbreviated as PrH), which is an isomerization product, and the other is n-propanol (hereinafter abbreviated as NPR), which is a hydrogenation product. In the step of extraction with water, these two by-products are extracted, together with unreacted allyl alcohol, into the aqueous phase. In the subsequent hydrogenation step, they are finally converted to NPR.

In carrying out the hydroformylation of allyl alcohol in a continuous process which includes the step of extraction with water, it is essential, from the industrial and economical standpoints, that all the following three requirements should be met:

(1) the selectivity toward HBA, which is the principal product, should be as high as possible;

(2) the amount of the rhodium complex that is dissolved in the aqueous extract layer should be as small as possible; and (3) the life of the rhodium complex catalyst should be maintained for an extended period of time.

The present inventors intensively investigated the dominant factors of the reaction, with respect to the above three requirements, and as a result they obtained the following new findings:

(a) when, as in the prior art, the apparent or manifest reaction conditions (carbon monoxide partial pressure, rhodium complex concentration, trisubstituted phosphine concentration, reaction temperature, etc.) alone are taken into consideration, the selectivity toward HBA, the main product, cannot exceed about 70% and that, for attaining a higher HBA selectivity, the rate of consumption of carbon monoxide, the amount of dissolved carbon monoxide in the reaction mixture and the rate of dissolution of carbon monoxide in the reaction mixture, amongst other factors, should be taken into consideration as well;

(b) the dissolution of the rhodium complex into the aqueous extract layer depends not only on the concentration of the total organic matter in the aqueous extract layer and the trisubstituted phosphine concentration relative to the rhodium complex, as is known in the prior art, but also on the concentration of unreacted allyl alcohol, the rate of consumption of carbon monoxide, the amount of dissolved carbon monoxide in the reaction mixture and the rate of dissolution of carbon monoxide in the reaction mixture, amongst other factors; and (c) the life of the rhodium catalyst depends not only on the rhodium complex concentration, trisubstituted phosphine concentration, reaction temperature, residence time of the reaction mixture in the hydroformylation reaction vessel, etc., as is known in the prior art, but also on the above-mentioned rate of consumption of carbon monoxide, the amount of dissolved carbon monoxide in the reaction mixture and the rate of dissolution of carbon monoxide in the reaction mixture, amongst other factors.

Based on these new findings, the present inventors conducted further investigations to establish a reaction procedure which would meet the above-mentioned three requirements. As a result, they found that the control of the apparent reaction conditions, such as rhodium complex concentration, trisubstituted phosphine concentration, carbon monoxide partial pressure, reaction temperature, etc., as has been proposed in the prior art, is not sufficient, and that it is important to select and control the carbon monoxide partial pressure, the rate of consumption of carbon monoxide, reaction temperature, etc. in a mutually interrelated manner so as to be capable of meeting the above-mentioned three requirements. These findings have now led to the present invention.

Thus, in accordance with the invention, there is provided an improvement in the process for the continuous hydroformylation of allyl alcohol, which includes the steps of hydroformylating allyl alcohol with a gaseous mixture of hydrogen and carbon monoxide, in an aromatic hydrocarbon, in the presence of a rhodium complex and a trisubstituted phosphine in an amount in excess relative to that of said rhodium complex, separating hydroxybutyraldehydes from the resulting hydroformylation reaction mixture by extraction with an aqueous medium and recycling the extraction residue to the hydroformylation step as a catalyst-containing solution, in which improved process HBA can be produced with high selectivity, the dissolution of the rhodium complex into the aqueous extract layer can be markedly reduced and the catalytic activity of the rhodium complex can be maintained stable over a prolonged period of time, wherein the improvement comprises: the hydroformylation reaction is carried out under conditions such that the value of A, defined by formula (I), given below, is maintained within the range of 0.2 to 2.5 in substantially the entire reaction zone in which the hydroformylation reaction proceeds:

$$A = (5.67 - 3.129 \times 10^{-3}T + 3.08 \times 10^{-5}T^2) \cdot P_{co} - \alpha(\mu/T)^{0.5}(r_{co}/K_v) \tag{I}$$

wherein T is the reaction temperature (°K.) and is selected to be within the range of 323° K. to 353° K. (absolute temperature), $P_{co}$ is the logarithmic mean (in atmospheres, absolute) between the partial pressure of carbon monoxide in the feed gas entering the reactor in which the hydroformylation reaction is conducted and the partial pressure of carbon monoxide in the effluent gas leaving said reactor and is within the range of 0.01 to 1.0 absolute atmosphere, $\alpha$ is 3,500 for the cases in which mechanical stirring is performed within the reactor and 1,200 for all other cases, $\mu$ is the viscosity (centipoises, cp) of the reaction mixture at the reaction temperature and is selected to be within the range of 0.1 to 4.0 cp, $r_{co}$ is the rate (moles/liter·hour) of consumption of carbon monoxide in the hydroformylation reaction and is selected to be within the range of from 0.001 to 10 moles/liter·hour, and $K_v$ is the rate (millimoles/liter·hour) of absorption of oxygen in water as determined separately from and independently of the hydroformylation reaction by measuring the rate of oxidation of an aqueous sodium sulfite solution with air at 25° C. under atmospheric pressure in the reactor to be used for the hydroformylation reaction and is selected to be within the range of 5 to 500 millimoles/liter·hour, provided that in cases where the reactor in which the hydroformylation reaction is carried out comprises a plurality of reaction chambers, each reaction chamber is regarded as a single reactor and the above constant and variables should be selected accordingly for each reaction chamber.

The value of A defined by the above formula (I) is considered to be closely related to the amount of carbon monoxide present in the reaction mixture. By maintaining the value of A within the above-specified range, it has become possible for the first time to conduct the continuous hydroformylation of allyl alcohol in an industrially and economically advantageous manner. The industrial significance of the present invention is thus very great.

The rate of consumption of carbon monoxide as expressed by $r_{co}$ in the above formula (I) can be determined easily by measuring the rate of flow of the feed gas entering the hydroformylation reactor and that of the effluent gas leaving said reactor, as well as the carbon monoxide concentration in the feed gas and that in the effluent gas. The value of this $r_{co}$ can also be determined from the rate of feeding allyl alcohol into the hydroformylation reactor, the concentration of unreacted allyl alcohol in the reaction mixture and the selectivity of the hydroformylation reaction (total selectivity toward HBA and HMPA).

The value of $K_v$ is determined by measuring, independently of and separately from the hydroformylation reaction, the rate of oxidation of an aqueous sodium sulfite solution with air at 25° C. in the same reactor that is to be used for said hydroformylation reaction or in a reactor of the same type. The method of measurement for this purpose has already been established and the details thereof can be found, for instance in Industrial and Engineering Chemistry, Vol. 48, No. 12, pages 2209-2122 (1956). This $K_v$ value depends on the method of supplying the feed gas and the shape of the hydroformylation reactor and also is subject to the influence of the stirring power of the reactor, the shape of the impeller, the method of distribution of the feed gas, and so on. Therefore, in making the $K_v$ value determination, it is of course necessary to employ the same conditions as the hydroformylation reaction conditions, except that the same reactor that is to be used in the hydroformylation or a reactor of the same construction is charged with an aqueous sodium sulfite solution and that air is fed into said reactor, in place of the hydrogen-carbon monoxide mixed gas, at the same linear velocity as under the hydroformylation reaction conditions, while maintaining the inside temperature at 25° C., under atmospheric pressure. The measurement for determining the $K_v$ value for the hydroformylation reactor can also be conducted by using a reactor of the same type as the hydroformylation reactor but of smaller size.

The value of $\alpha$ is 3,500 in cases where mechanical stirring is performed within the hydroformylation reaction vessel by means of an impeller or the like, whereas it is 1,200 in cases where mechanical stirring is not performed, for instance, in the case of a bubble column.

The value of $\mu$, which is the viscosity of the reaction mixture at the reaction temperature, can be determined by conventional methods.

In the present invention, it is required to select the values of T, $P_{co}$, $\mu$, $r_{co}$ and $K_v$ interrelatedly within the respective ranges specified hereinabove so that the value of A defined by formula (I) can be maintained within the range of 0.2 to 2.5 in substantially the entire zone in which the hydroformylation reaction proceeds. By taking the above measures, markedly improved effects, such as those mentioned above, can be produced. If the value of A is smaller than 0.2, the rate of formation of PrH and NPR tends to increase and the rate of the desired reaction tends to decrease, hence the yield of HBA tends to decrease. In that case, the life of the rhodium complex catalyst also tends to be shortened. If, conversely, the value of A exceeds 2.5, then the selectivity toward HMPA tends to increase and the selectivity towards HBA tends to decrease. In this case, the loss of the rhodium complex by dissolution into the aqueous extract layer in the extraction step shows a tendency to increase.

In practicing the present invention, any rhodium complex which is capable of catalyzing the hydroformylation reaction and is slightly soluble or insoluble in water can be used as the aforementioned rhodium complex. While a large number of such rhodium complexes are known, rhodium complexes represented by the formula $HRh(CO)(PR_3)_3$ wherein R is an aryl group, and rhodium carbonyl cluster complexes are preferred from the viewpoints of catalytic activity, solubility and ease of handling. Typical rhodium complexes are $HRh(CO)(PPh_3)_3$,
wherein Ph is phenyl, $HRh(CO)[P(C_6H_4CH_3)_3]_3$, $Rh_4(CO)_{12}$ and $Rh_6(CO)_{16}$ amongst others. The rhodium complex is generally used in an amount of 0.25 to 2.5 milligram atoms per liter of the hydroformylation reaction mixture as expressed on the rhodium atom basis.

In carrying out the reaction according to the present invention, the concentration of the trisubstituted phosphine in the reaction mixture is maintained generally within the range of 50 to 300 mole equivalents, preferably 75 to 200 mole equivalents, per gram atom of rhodium in the rhodium complex. While a variety of trisubstituted phosphines can be used, it is preferred to use trisubstituted monophosphines which are represented by the general formula $PR'R''R'''$ wherein R', R" and R'" are the same or different and each is an aryl group. Examples are triphenylphosphine, trinaphthylphosphine and tritolylphosphine. Among them, triphenylphosphine is most preferred from the viewpoints of availability, minimal loss by dissolution into the aqueous extract layer, stability, and so forth.

The solvent to be used in the practice of the present invention is an aromatic hydrocarbon. Preferred solvents are benzene, toluene and xylene, which are capable of sufficiently dissolving the rhodium complex and trisubstituted phosphine.

Allyl alcohol is preferably fed into the hydroformylation reaction zone at a rate such that the concentration of hydroxybutyraldehydes in the hydroformylation reaction mixture is maintained within the range of 0.5 to 3 moles per liter. It is advantageous that the final conversion of allyl alcohol should be not less than 90%, preferably not less than 97%, so that the loss of allyl alcohol by conversion thereof to NPR in the subsequent hydrogenation step can be minimized. The residence time of the reaction mixture within the hydroformylation reaction vessel is selected to be within the range of 1 to 10 hours so that the conversion of allyl alcohol can reach the above-mentioned range.

The reaction pressure in the hydroformylation reaction is preferably not higher than 10 atmospheres (absolute pressure). The hydrogen/carbon monoxide partial pressure ratio in the feed gas is selected to be within the range of 1/1 to 30/1. In cases where the feed gas is supplied in divided streams to the reactor, the above partial pressure ratio should be taken into consideration as well and should be maintained in the above-described range for the reactor considered as a whole. A gas inert to the hydroformylation reaction, such as nitrogen, helium, argon or methane, may be present in the reaction zone.

As has already been proposed by some of the present inventors (cf. U.S. Pat. No. 4,215,077), a diphosphinoalkane represented by the general formula

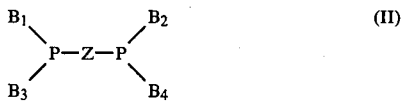

wherein $B_1$, $B_2$, $B_3$ and $B_4$ are the same or different and each is an aryl group, and Z is a divalent hydrocarbon group containing 2 to 5 carbon atoms in the main chain thereof and which may optionally be substituted by a lower alkyl group or groups, can be present along with the trisubstituted phosphine in the hydroformylation reaction mixture. The diphosphinoalkane can contribute to stabilization of the rhodium complex catalyst and further prolongation of the catalyst life. In the continuous hydroformylation of allyl alcohol in accordance with the present invention, the concentration of the diphosphinoalkane is desirably maintained within the range of 0.025 to 0.75 mole equivalents per gram atom of rhodium contained in the rhodium complex. The diphosphinoalkane is partly lost by dissolution into the aqueous extract layer or by oxidation with oxygen contained in a trace amount in the feed gas. Accordingly, it is desirable to supply make-up amounts of the same, either continuously or intermittently, so that its concentration can be maintained within the above range. Among the large number of diphosphinoalkanes which are usable, some typical examples are given below.

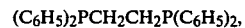

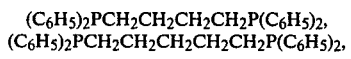

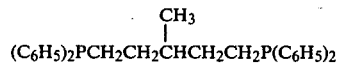

Among such diphosphinoalkanes, -1,4-bis(diphenylphosphino)butane is most preferred from the viewpoints of the hydroformylation reaction rate, HBA selectivity, catalytic activity-maintaining effect, availability, and so on.

As mentioned hereinabove, the value of $K_v$ in the above formula (I) depends on the shape of the reactor. Therefore, in the practice of the present invention, the kind of reactor to be used should desirably be taken into consideration as well. The reactors usable in the practice of the invention are roughly classifiable into two groups. One includes stirred-tank reactors (single-stage or multistage) and the other includes bubble-tower reactors (vertical or horizontal type, single-stage, compartment type, or multistage). The combined use of two or more reactors can result in a reduction of the total reactor volume and in a high allyl alcohol conversion with the residence time being shortened. The combination of reactors can be selected at will. For instance, there can be considered the combined use of bubble-tower reactors alone or the use of a stirred-tank reactor as the first reactor and a bubble-tower reactor(s) as the second (and subsequent) reactor(s). The use of a stirred-tank reactor as the first reactor makes it easy to control the value of A defined by formula (I) within the range of 0.2 to 2.5, and, as a result, a high HBA selectivity can be attained and the loss by dissolution of the rhodium complex can be minimized. Stirred-tank reactors are better with regard to the ease of removal of the heat of reaction, ease of adjustment of the production rate, stability in operation, and so forth. Furthermore, the use of a bubble-tower reactor(s) as the second (and subsequent) reactor(s) makes it possible, in particular, to attain a high allyl alcohol conversion with the total reactor capacity being reduced as a whole and the residence time being shortened.

After the hydroformylation reaction, the reaction mixture is extracted with an aqueous medium for the separation of hydroxybutyraldehydes therefrom, and the extraction residue, containing the catalyst component, is recycled to the hydroformylation reaction step. In the conventional cases, water is used as the aqueous medium for said extraction. The aqueous medium may optionally contain other extraction components or substantially inert components. 1,4-BG or/and MPG are typical of such optional components and they may be used to replace not more than 30 percent of the water used for the extraction. In the extraction step, the aqueous medium is used in an amount selected from within the range of from 0.5 to 1.5 parts by volume, per one part by volume of the hydroformylation reaction mixture.

The extraction apparatuses that can be used for the extraction procedure include agitated-column extractors (mixer-settlers, RDC (rotating-disk contractor), etc.) and plate-column extractors (perforated-plate columns, etc.) which are in conventional use. Generally, the extraction is carried out in an atmosphere consisting of an inert gas (e.g., nitrogen, helium, argon), gaseous hydrogen, a gaseous mixture of hydrogen and carbon monoxide, or the like, within the temperature range of 0° C. to 50° C., preferably 5° C. to 30° C.

The aqueous extract layer containing hydroxybutyraldehydes, obtained by the process according to the present invention, upon hydrogenation, gives an aqueous solution of 1,4-BG and MPG. 1,4-BG and MPG each can be isolated from said aqueous solution by any conventional separation procedure. The water can be recycled to the extraction step for reuse. 1,4-BG obtainable in this way is useful as a raw material for the production of polyurethanes or as an intermediate for synthesizing a variety of industrially useful compounds.

Figure 1:
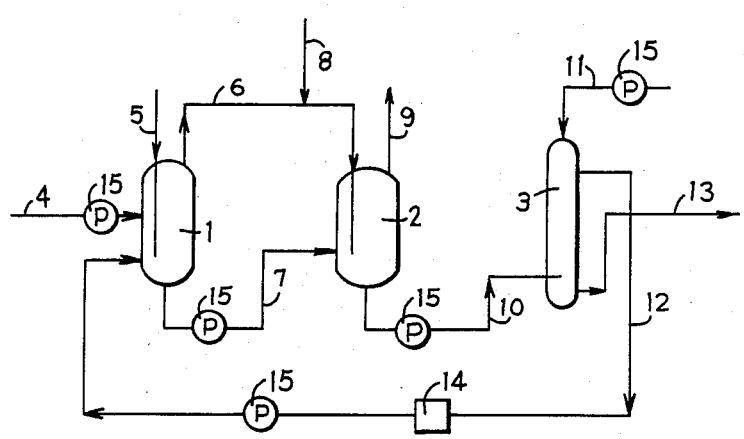
FIG. 1 is the flowchart illustrating the reaction described in Example 1.

In the drawings, the reference numbers identify parts as follows: 1,2 . . . hydroformylation reactors; 3 . . . extraction column; 4 to 13 . . . conduits; 14 . . . catalyst solution reservoir; 15 . . . constant-flow pump; 21 . . . reactor; 22 . . . first reaction chamber; 23 . . . 9th reaction chamber; 24 . . . circulating gas cooler; 25 . . . gas reservoir; 26 . . . compressor; 27 . . . allyl alcohol reservoir; 28 . . . reaction mixture cooler; 29 . . . extraction column; 30 . . . catalyst solution reservoir; 31 . . . reaction product reservoir; 32 to 34 . . . constant-flow pumps; 35 to 39 . . . flowmeters; 40 . . . pressure-adjusting valve; 41,42 . . . flow rate-adjusting valves; 51 . . . reactor; 52,53 . . . gas flowmeters; 54 . . . constant-flow pump; 55 . . . pressure gauge; 56 . . . compressor; 57 . . . filter; 58 . . . feed reservoir; 59 . . . flow rate-adjusting valve.

The following examples illustrate the present invention in more detail.

EXAMPLE 1

Allyl alcohol was hydroformylated in a continuous manner according to the flowchart shown in FIG. 1.

Reactor (1) was a 5.5-liter reactor (108.3 mm in diameter, 600 mm in height) equipped with a magnetic stirrer, reactor (2) was a 10-liter reactor (130.8 mm in diameter, 750 mm in height) equipped with a magnetic stirrer, and extraction column (3) was a 2.2-liter agitated-column extractor. Each reactor was fitted with an external jacket so that the reactor internal temperature could be maintained at a constant level by causing water warmed to the intended temperature to flow through said jacket.

Determination of $K_\nu$ values for the reactors

The $K_\nu$ values for reactors (1) and (2) were determined at different rates of stirring. Thus, reactor (1) was charged with 3.5 liters of an aqueous solution containing 0.5 mole/liter of sodium sulfite and 10 millimoles/liter of copper sulfate, and air was introduced under atmospheric pressure at the rate of 130 Nl/hour while maintaining the internal temperature at 25° C. Stirring was performed at the rate given in Table 1, and 10-ml reaction mixture samples were taken at 10-minute intervals and assayed for sodium sulfite by titration with aqueous sodium thiosulfate. The reaction was continued for 60 minutes. Based on the reaction time-versus-sodium sulfite concentration relationship thus found, the rate of oxidation of sodium sulfite was determined. The $K_\nu$ values for reactor (2) were determined by proceeding in the same manner as for reactor (1), except that the reactor was charged with 7 liters of the aqueous sodium sulfite solution and that the rate of feeding air was 90 Nl/hour. The results obtained are shown in Table 1.

TABLE 1

|  | Rate of stirring (rpm) | Value of $K_\nu$ (millimoles/l · hour) |
|---|---|---|
| Reactor (1) | 480 | 29 |
|  | 570 | 50 |
| Reactor (2) | 800 | 40 |
|  | 850 | 50 |

Hydroformylation reaction

The entire reaction system was charged with 13 liters of a toluene solution containing 1 millimole/liter of RhH(CO)(PPh$_3$)$_3$, 150 millimoles/liter of PPh$_3$ and 0.2 millimole/liter of Ph$_2$P(CH$_2$)$_4$PPh$_2$, from the catalyst solution reservoir (14). Allyl alcohol was fed to the reactor (1) at the rate of 3 moles/hour and hydrogen and carbon monoxide were fed to the reactor (1) at the rates of 235 Nl/hour and 65 Nl/hour, respectively, through the line (4). The reaction mixture was transferred to reactor (2) through line (7) at the rate of 1.7 liters/hour so that the quantity of the reaction mixture in reactor (1) was maintained at 3.5 liters. The temperature and pressure within reactor (1) were maintained at 60° C. and 2.1 atmospheres (absolute), respectively, and stirring was conducted at the rate of 570 rpm. The effluent gas from reactor (1) was sent to reactor (2) through line (6). Carbon monoxide was fed to reactor (2) through line (8) at the rate of 10 Nl/hour. The effluent gas from reactor (2) was discharged from the system through line (9). While maintaining the quantity of the reaction mixture in reactor (2) at 7 liters, the reaction mixture was sent to extraction column (3) through line (10) at the rate of 1.7 liters/hour. The temperature and pressure within reactor (2) were maintained at 60° C. and 2.0 atmospheres (absolute), respectively, and stirring was conducted at the rate of 800 rpm. Water was fed to extraction column (3) through line (11) at the rate of 1.5 liters/hour and the extraction was performed at 30° C. in a hydrogen atmosphere. The extraction residue containing the catalyst components was recycled to reactor (1), at the rate of 1.5 liters/hour, through line (12) and catalyst solution reservoir (14). The aqueous extract layer was taken out of the system through line (13).

When the reaction had reached steady-state operation, the rate of flow of the effluent gas from reactor (1) was 194 Nl/hour as measured in line (6), the carbon monoxide concentration in said effluent gas was 6.8 vol. %, the carbon monoxide concentration in the gas entering reactor (2) was 11.3 vol. %, the rate of flow of the effluent gas from reactor (2) was 186 Nl/hour as measured in line (9) and the carbon monoxide concentration in said effluent gas was 7.6 vol. %. From these values, the P$_{co}$ values for reactors (1) and (2) were calculated to be 0.270 atmosphere (absolute) and 0.187 atmosphere (absolute), respectively, and the r$_{co}$ values for reactors (1) and (2) to be 0.661 mole/liter·hour and 0.0577 mole/liter·hour, respectively. The viscosity of the reaction mixture at 60° C. was found to be 0.4 cp by actual measurement. From these data, the values of A for reactors (1) and (2) were calculated to be 0.57 and 1.33, respectively.

After assaying for allyl alcohol, NPR and PrH by gas chromatography, the aqueous extract layer was hydrogenated, in the presence of Raney nickel catalyst, at 100 atmospheres and 60° C., followed by assaying for the products 1,4-BG and MPG. Based on the data thus obtained, the conversion of allyl alcohol and the selectivity to each product were determined. The results obtained are shown below. In a separate experiment, it was confirmed that HBA and HMPA are quantitatively converted to 1,4-BG and MPG, respectively, under the hydrogenation conditions mentioned above.

| Allyl alcohol conversion | 98% |
|---|---|
| Product selectivity (mole %) | |
| HBA | 79.1 |
| HMPA | 11.3 |
| PrH | 6.4 |
| NPR | 3.2 |

On the basis of the results of analysis of RhH(CO)(PPh$_3$)$_3$, PPh$_3$ and Ph$_2$P(CH$_2$)$_4$PPh$_2$ in the extraction residue by atomic absorption photometry and liquid chromatography, RhH(CO)(PPh$_3$)$_3$, PPh$_3$ and Ph$_2$P(CH$_2$)$_4$PPh$_2$ were added together with toluene in appropriate amounts so that their concentrations could be maintained within the ranges of 0.99–1.01 millimoles/liter, 145–150 millimoles/liter and 0.18–0.2 millimole/liter, respectively. The reaction was performed continuously for 30 days. The allyl alcohol conversion was constant at 98% throughout the reaction period, with no changes in selectivity to each product. The dissolution of the rhodium complex into the aqueous extract layer always remained within the range of 8–10 ppb (as rhodium metal) as determined by atomic absorption photometry.

COMPARATIVE EXAMPLES 1, 2 and 3

The hydroformylation of allyl alcohol was conducted for 14 or 18 days under the same conditions as described in Example 1 except that the rate of stirring, the total reaction pressure and the carbon monoxide concentration in the feed gas were varied for each reactor as given in Table 2. In Comparative Example 3, carbon monoxide was supplied through line (8) at the rate of 30 Nl/hour. In each reaction, the total rate of flow of hydrogen and carbon monoxide to reactor (1) was adjusted to 300 Nl/hour.

The allyl alcohol conversion and selectivity to each product were determined in the same manner as described in Example 1 by analysis of the aqueous extract layer. The results of the reaction and the data for the dissolution of the rhodium complex into the aqueous extract layer are shown in Table 3, and the calculated values of A are shown in Table 4. In Comparative Example 1 and Comparative Example 3, it was revealed that the catalytic activity decreased by about 0.5% daily. In Comparative Example 2, the rhodium complex was dissolved into the aqueous extract layer in increased amounts and a decreasing tendency of the allyl alcohol conversion was noted.

TABLE 2

| | | Rate of stirring (rpm) | Reaction pressure (atmospheres, absolute) | Carbon monoxide concentration feed gas (%) | Reaction time (days) |
|---|---|---|---|---|---|
| Comparative Example 1 | Reactor 1 | 570 | 1.4 | 20.0 | 14 |
| | Reactor 2 | 800 | 1.3 | 10.9 | |
| Comparative Example 2 | Reactor 1 | 570 | 2.3 | 30.0 | 14 |
| | Reactor 2 | 800 | 2.2 | 23.7 | |
| Comparative Example 3 | Reactor 1 | 480 | 2.1 | 21.7 | 18 |
| | Reactor 2 | 850 | 2.0 | 21.8 | |

TABLE 3

| | Effluent gas flow rate (Nl/hr) | | CO concentration in effluent gas (%) | | Allyl alcohol conversion rate at early stage of reaction (%) | Selectivity (mole %) | | | | Dissolution of rhodium (ppb, as Rh metal) |
|---|---|---|---|---|---|---|---|---|---|---|
| | Reactor 1 | Reactor 2 | Reactor 1 | Reactor 2 | | HBA | HMPA | PrH | MPR | |
| Comparative Example 1 | 208 | 200 | 7.6 | 8.4 | 97 | 71.9 | 9.1 | 12.0 | 7.0 | 10–12 |
| Comparative Example 2 | 196 | 189 | 19.9 | 21.7 | 98 | 71.8 | 19.2 | 4.9 | 4.1 | 30–35 |
| Comparative Example 3 | 206 | 218 | 9.6 | 18.6 | 98 | 71.0 | 12.0 | 12.1 | 4.9 | 25–30 |

TABLE 4

| | | Kv (millimoles/l · hour) | Pco (atmospheres, absolute) | rco (moles/l · hour) | μ (cp) | A |
|---|---|---|---|---|---|---|
| Comparative Example 1 | Reactor 1 | 50 | 0.182 | 0.563 | 0.4 | 0.10 |
| | Reactor 2 | 40 | 0.125 | 0.0585 | 0.4 | 0.83 |
| Comparative Example 2 | Reactor 1 | 50 | 0.567 | 0.647 | 0.4 | 2.99 |
| | Reactor 2 | 40 | 0.499 | 0.0518 | 0.4 | 3.86 |
| Comparative Example 3 | Reactor 1 | 29 | 0.312 | 0.576 | 0.4 | 0.10 |
| | Reactor 2 | 50 | 0.396 | 0.0591 | 0.4 | 3.04 |

EXAMPLE 2

Figure 2:
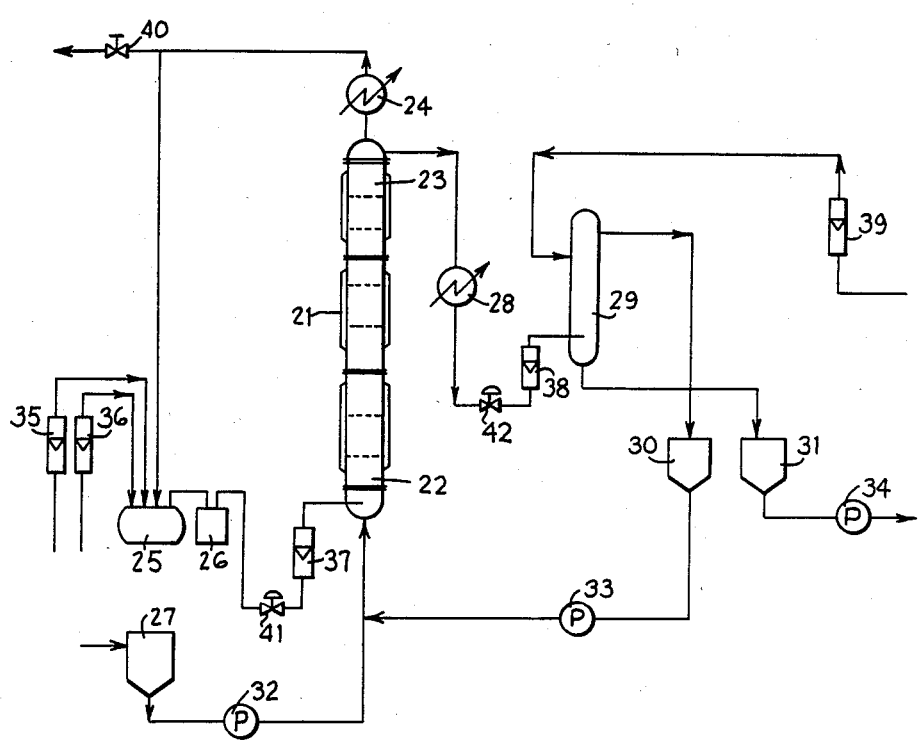
FIG. 2 is a flowchart illustrating the reaction described in Example 2.

The hydroformylation of allyl alcohol was conducted continuously in accordance with the flowchart illustrated in FIG. 2.

Reactor (21) was a multistage bubble-tower reactor, 100 mm in diameter and about 5 meters in height, composed of three 1.5 m-long reactor sections equipped with flanges, and top and bottom end plates. Perforated plates were disposed within the reactor so that the reactor consisted of a total of 9 reaction chambers. The reactor was fitted with sampling nozzles, thermometer nozzles and an external jacket. The interior of the reactor could be maintained at a constant temperature by flowing water warmed to the intended temperature through said jacket. The quantity of the reaction mixture within the reactor could be adjusted within the range of 30–40 liters by adjusting the position of a reaction mixture overflow nozzle. In this way, the allyl alcohol conversion could be adjusted. Extraction column (29) was an agitated-column extractor, 80 mm in diameter and 1.5 m in the length of the extraction-effecting portion.

Measurement of $K_\nu$ values for the reaction chambers

Figure 3:
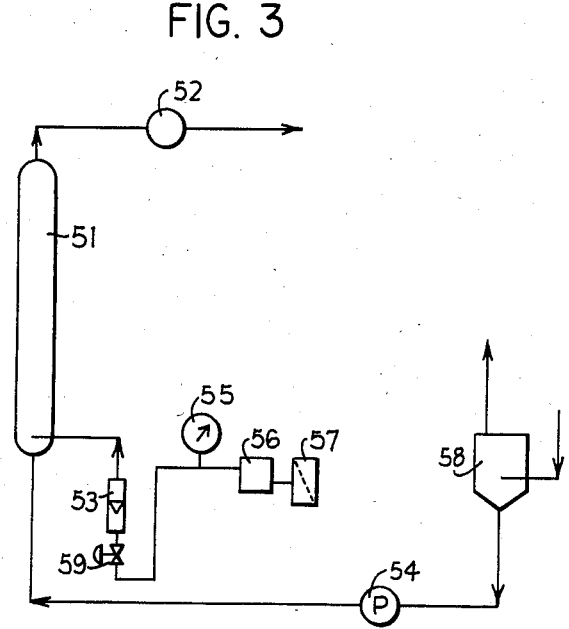
FIG. 3 is a flowchart illustrating how the $K_\nu$ value determination in Example 2 was performed.

Using reactor (21), the $K_\nu$ value determination was performed according to the flowchart illustrated in FIG. 3. An aqueous solution containing copper sulfate and sodium sulfite, each in the same concentration as in Example 1, was deaerated with nitrogen in reservoir (58) and fed to the reactor through metering pump (54). While maintaining the reactor interior temperature at 25° C., air was fed to the reactor under atmospheric pressure by means of compressor (56), and $K_\nu$ values were determined in the same manner as described in Example 1.

Hydroformylation reaction

The hydroformylation of allyl alcohol was carried out under the conditions given in Table 5.

A toluene solution containing 1 millimole/liter of $RhH(CO)(PPh_3)_3$, 150 millimoles/liter of $PPh_3$ and 0.1 millimole/liter of $Ph_2P(CH_2)_4PPh_2$ was fed from catalyst solution reservoir (30) to the reactor through constant-flow pump (33) at the rate of 13.64 liters/hour. The interior temperature of reactor (21) was maintained at 60.5° C. The feed gas, which had the composition given in Table 5, was pressurized to 2.6 atmospheres (absolute) by means of compressor (26) and fed to the reactor at the rate of 3.93 $Nm^3$/hour. Allyl alcohol was fed to the reactor from allyl alcohol reservoir (27) through constant-flow pump (32) at the rate of 2.18 liters/hour. The reaction mixture was allowed to overflow a nozzle fitted to the reactor at the upper part thereof. The overflow was cooled in cooler (28) and then sent to extraction column (29). Water was fed to the extraction column at the rate of 14.5 liters/hour, and the extraction was conducted under a nitrogen atmosphere.

The aqueous layer resulting from the extraction was temporarily stored in reaction product reservoir (31) and sent to the next hydrogenation step through constant-flow pump (34). The extraction residue containing the catalyst components was taken out from the top of the extraction column and transferred into catalyst solution reservoir (30) and therefrom recycled to the reactor through constant-flow pump (33). The catalyst solution to be recycled was analyzed for $RhH(CO)(PPh_3)_3$, $PPh_3$ and $Ph_2P(CH_2)_4PPh_2$ and, according to the assay results, $RhH(CO)(PPh_3)_3$, $PPh_3$ and $Ph_2P(CH_2)_4PPh_2$ were added together with toluene in necessary amounts so that their concentrations in said catalyst solution were maintained at 1 millimole/liter, 145–150 millimoles/liter and 0.08–0.10 millimole/liter, respectively. The effluent gas leaving the reactor from the top thereof was cooled in cooler (24) so as to recover condensable accompanying material. Part of the gas was released from the system and the remaining portion was returned to gas reservoir (25), where the consumptions of materials in the reaction and the losses by release were made up. The gas so adjusted was pressurized by means of compressor (26) and fed to the reactor.

After the reaction reached a steady-state condition, the reaction mixture was sampled, and the allyl alcohol conversion and the selectivities to HBA, HMPA, PrH and NPR were determined. Separately, the aqueous layer obtained by extraction was hydrogenated and the product was analyzed for 1,4-BG, MPG and NPR, and, based on the yields of 1,4-BG and MPG as found in that manner, the selectivities to HBA, HMPA, PrH and NPR were calculated. The selectivity values thus obtained were in agreement with the selectivity values data obtained by the direct gas chromatographical analysis of the reaction mixture from the reactor. The dissolution of the rhodium complex into the aqueous extract layer was determined by atomic absorption photometry.

The reaction was carried out continuously for 40 days. The values obtained for each analytical item, excluding the maximum and minimum values, were averaged arithmetically. The results thus obtained are shown in Table 6. Throughout the reaction period, a decrease in catalytic activity was not noted at all.

The gas leaving the reactor was analyzed for its composition, and the carbon monoxide partial pressure and hydrogen partial pressures at the outlet of the reactor were calculated. The pressure of the gaseous layer which formed under each perforated plate in the reactor and the composition thereof were measured or determined, and the carbon monoxide partial pressure and hydrogen partial pressure in each reaction chamber were measured. Based on the thus-obtained analytical results, the rate of consumption of carbon monoxide in each reaction chamber was calculated. The calculated values of $K_\nu$ and A for the first and ninth reaction chambers as obtained in the above calculations are shown in Table 7.

COMPARATIVE EXAMPLES 4 AND 5

Following the same procedure as described in Example 2, the hydroformylation of allyl alcohol was carried out continuously for 20 days under the conditions given in Table 5. In Comparative Example 4, $RhH(CO)(PPh_3)_3$ was used in the concentration of 1.34 millimoles/liter.

In each example, the allyl alcohol conversion at an early stage of reaction, the selectivity to each product and the dissolution of rhodium complex into the aqueous extract layer were as shown in Table 6. The $K_\nu$ values for the first and ninth reaction chambers and the A values calculated are shown in Table 7. In Comparative Example 5, the catalytic activity was found to decrease by about 0.7% daily. In Comparative Example 4, an increased dissolution of rhodium complex into the aqueous extract layer as well as a decrease in allyl alcohol conversion were noted.

TABLE 5

| | Reaction temperature (°C.) | Reaction pressure (atmospheres, absolute) | | Allyl alcohol feeding rate (liters/hour) | Catalyst solution feeding rate (liters/hour) | Feed gas flow rate (Nm³/hour) | Feed gas composition (vol. %) | | |
|---|---|---|---|---|---|---|---|---|---|
| | | Tower top | Tower bottom | | | | $H_2$ | CO | Inert gas |
| Example 2 | 60.5 | 2.4 | 2.6 | 2.18 | 13.64 | 3.93 | 77.8 | 18.5 | 3.7 |
| Comparative Example 4 | 64.5 | 2.4 | 2.8 | 2.35 | 13.69 | 4.10 | 69.3 | 28.4 | 2.3 |
| Comparative Example 5 | 64.0 | 2.0 | 2.4 | 2.23 | 13.75 | 3.10 | 84.8 | 12.0 | 3.2 |

TABLE 6

| | Allyl alcohol conversion rate at early stage of reaction (%) | Selectivity (mole %) | | | | Dissolution of rhodium ppb, as Rh metal) |
|---|---|---|---|---|---|---|
| | | HBA | HMPA | PrH | NPR | |
| Example 2 | 90.0 | 79.0 | 11.0 | 7.8 | 2.2 | 10 |
| Comparative Example 4 | 98.1 | 71.5 | 22.8 | 4.3 | 1.4 | 40 |
| Comparative Example 5 | 89.4 | 71.9 | 7.8 | 11.8 | 8.5 | 10 |

TABLE 7

| | | Kv (millimoles/ l · hour) | μ (cp) | CO concentration (volume %) | | CO partial pressure (atmospheres, absolute) | | Pco (atmospheres, absolute) | rco (mole/ l · hour) | A |
|---|---|---|---|---|---|---|---|---|---|---|
| | | | | Inlet | Outlet | Inlet | Outlet | | | |
| Example 2 | 1st reaction chamber | 56 | 0.40 | 18.5 | 14.4 | 0.48 | 0.36 | 0.42 | 2.37 | 1.61 |
| | 9th reaction chamber | 44 | | 6.6 | 5.2 | 0.135 | 0.104 | 0.12 | 0.47 | 0.50 |
| Comparative Example 4 | 1st reaction chamber | 57 | 0.38 | 28.4 | 23.3 | 0.795 | 0.63 | 0.71 | 1.94 | 4.3 |
| | 9th reaction chamber | 42 | | 16.5 | 16.2 | 0.40 | 0.39 | 0.395 | 0.11 | 3.1 |
| Comparative Example 5 | 1st reaction chamber | 44 | 0.38 | 12.0 | 7.7 | 0.288 | 0.18 | 0.23 | 1.85 | 0.15 |
| | 9th reaction chamber | 38 | | 0 | 0 | 0 | 0 | 0 | 0 | 0 |

We claim:

1. In the process of continuous hydroformylation of allyl alcohol which includes the steps of, in a reactor, hydroformylating allkyl alcohol with a gaseous mixture of hydrogen and carbon monoxide, in an aromatic hydrocarbon selected from the group consisting of benzene, toluene and xylene, in the presence of a rhodium complex selected from the group consisting of a rhodium complex of the formula H Rh(Co)(PR₃)₃, wherein R is an aryl group, and a rhodium carbonyl cluster complex, and in the presence of a trisubstituted phosphine in an amount in excess of the amount of said rhodium complex, then separating hydroxybutyraldehydes from the resulting hydroformylation reaction mixture by extraction with an aqueous medium and recycling the extraction residue to the hydroformylation step as a catalyst-containing solution, the improvement which comprises: the hydroformylation reaction is continuously carried out under conditions such that the value of A defined by formula (I) given below is maintained within the range of 0.2 to 2.5 in substantially the entire reaction zone in which the hydroformylation reaction proceeds:

$$A = (5.67 - 3.129 \times 10^{-3}T + 3.08 \times 10^{-5}T^2) \cdot P_{co} - \alpha(\mu/T)^{0.5}(r_{co}/K_V) \quad (I)$$

where T is the reaction temperature, in °K. and is within the range of 323° K. to 353° K., $P_{co}$ is the logarithmic mean (in atmospheres absolute) between the partial pressure of carbon monoxide in the feed gas entering the reactor in which the hydroformylation reaction is conducted and the partial pressure of carbon monoxide in the effluent gas leaving said reactor and is within the range of 0.01 to 1.0 absolute atmosphere, α is 3,500 for cases where mechanical stirring is performed within the reactor and 1,200 for all other cases, is the viscosity (cp) of the reaction mixture at the reaction temperature and is within the range of 0.1 to 4.0 cp, $r_{co}$ is the rate (moles/liter·hour) of consumption of carbon monoxide in the hydroformylation reaction and is within the range of 0.001 to 10 moles/liter·hour, and $K_v$ is the rate (millimoles/liter·hour) of absorption of oxygen in water as determined separately and independently of the hydroformylation reaction by measuring the rate of oxidation of an aqueous sodium sulfite solution with air at 25° C. under atmospheric pressure in the reactor to be used for the hydroformylation reaction and $K_v$ is within the range of 5 to 500 millimoles/liter·hour, provided that in cases where the reactor in which the hydroformylation reaction is carried out comprises a plurality of reaction chambers, each reaction chamber is regarded as a single reactor and the above constant and variables are selected accordingly.

2. The improvement according to claim 1, wherein the trisubstituted phosphine is triphenylphosphine.

3. The improvement according to claim 1, wherein the rhodium complex concentration in the reaction mixture as expressed on the rhodium atom basis is 0.25 to 2.5 milligram atoms per liter and the trisubstituted phosphine concentration is 50 to 300 mole equivalents per gram atom of rhodium contained in the rhodium complex.

4. The improvement according to claim 1, wherein a diphosphinoalkane represented by the formula

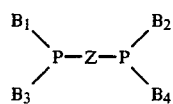

(II)

wherein $B_1$, $B_2$, $B_3$ and $B_4$ are the same or different and each is an aryl group, and Z is a hydrocarbon group containing 2 to 5 carbon atoms in the main chain thereof which may optionally be substituted by a lower alkyl group or groups, is present in addition to the trisubstituted phosphine in the reaction mixture and the concentration thereof is maintained within the range of 0.025 to 0.75 mole equivalent per gram atom of rhodium contained in the rhodium complex.

5. The improvement according to claim 4, wherein the diphosphinoalkane of general formula (II) is 1,4-bis(diphenylphosphino)butane.

6. The improvement according to claim 1, wherein said rhodium complex is selected from the group consisting of $HRh(CO)(PPh_3)_3$ wherein Ph is phenyl, $HRh(CO)[P(C_6H_4CH_3)_3]_3$, $Rh_4(CO)_{12}$ and $Rh_6(CO)_{16}$.

* * * * *

UNITED STATES PATENT AND TRADEMARK OFFICE
CERTIFICATE OF CORRECTION

PATENT NO. : 4 567 305
DATED    : January 28, 1986
INVENTOR(S) : Mitsuo MATSUMOTO et al It is certified that error appears in the above-identified patent and that said Letters Patent is hereby corrected as shown below:

Column 13, line 56; change "Co" to ---CO---.
Column 14, line 49; after "cases," insert ---µ---.

Signed and Sealed this

Eighth Day of July 1986

[SEAL]

Attest:

DONALD J. QUIGG

Attesting Officer

Commissioner of Patents and Trademarks